(12) United States Patent
Winterfield

(10) Patent No.: US 9,399,026 B2
(45) Date of Patent: Jul. 26, 2016

(54) METHODS FOR ALLEVIATING STATIN MYOPATHY

(71) Applicant: Roland W. Winterfield, Hinsdale, IL (US)

(72) Inventor: Roland W. Winterfield, Hinsdale, IL (US)

(*) Notice: Subject to any disclaimer, the term of this patent is extended or adjusted under 35 U.S.C. 154(b) by 0 days.

(21) Appl. No.: 14/853,374

(22) Filed: Sep. 14, 2015

(65) Prior Publication Data

US 2016/0008304 A1    Jan. 14, 2016

Related U.S. Application Data

(63) Continuation of application No. PCT/US2015/023102, filed on Mar. 27, 2015.

(60) Provisional application No. 61/971,072, filed on Mar. 27, 2014.

(51) Int. Cl.

| A61K 31/19 | (2006.01) |
| A01N 37/00 | (2006.01) |
| A61K 31/21 | (2006.01) |
| A61K 31/366 | (2006.01) |
| A61K 31/40 | (2006.01) |
| A61K 31/4418 | (2006.01) |
| A61K 31/505 | (2006.01) |
| A61K 31/22 | (2006.01) |
| A61K 31/405 | (2006.01) |
| A61K 31/47 | (2006.01) |

(52) U.S. Cl.
CPC ............ *A61K 31/19* (2013.01); *A61K 31/22* (2013.01); *A61K 31/366* (2013.01); *A61K 31/40* (2013.01); *A61K 31/405* (2013.01); *A61K 31/4418* (2013.01); *A61K 31/47* (2013.01); *A61K 31/505* (2013.01)

(58) Field of Classification Search
CPC ... A61K 2300/00; A61K 31/19; A61K 31/22; A61K 31/366; A61K 31/40; A61K 31/405; A61K 31/4418; A61K 31/47; A61K 31/505
USPC .......................... 514/275, 423, 460, 510, 557
See application file for complete search history.

(56) References Cited

U.S. PATENT DOCUMENTS

| 5,360,613 A | 11/1994 | Nissen |
| 2004/0132802 A1 | 7/2004 | Butler et al. |
| 2010/0179112 A1 | 7/2010 | Rathmacher et al. |
| 2013/0017283 A1 | 1/2013 | Zemel et al. |
| 2014/0249223 A1* | 9/2014 | Pedrosa .................... A23L 1/30 514/557 |

FOREIGN PATENT DOCUMENTS

| EP | 2322146 | 5/2011 |
| WO | WO 2012112419 A1 * | 8/2012 ................ A23L 1/30 |

OTHER PUBLICATIONS

Aversa et al., "Beta-hydroxy-beta-methylbutyrate (HMB) attenuates muscle and body weight loss in experimental cancer cachexia." Int. J. Oncol. 38:713-20, 2011.
Aversa et al., "β-Hydroxy-β-methylbutyrate (HMB) prevents dexamethasone-induced myotube atrophy." Biochem. Biophys. Res. Comm. 423(4):739-43, 2012.
Chan et al., "Differential association between statin exposure and elevated levels of creatine kinase." Ann. Pharmacother. 39:1611-16, 2005.
Dirks & Jones, "Statin-induced apoptosis and skeletal myopathy." Am. J. Physiol. Cell Physiol. 291:C1208-12, 2006.
International Search Report from International Application No. PCT/US2015/023102, mailed Jun. 26, 2015.
Liao, "Squalene synthase inhibitor lapaquistat acetate. Could anything be better than statins?" Circulation 123:1925-28, 2011.
Nissen et al., "Beta-hydroxy-beta-methylbutyrate (HMB) supplementation in humans is safe and may decrease cardiovascular risk factors." J. Nutrition 130(8):1937-45, 2000.
Rosanoff & Seelig, "Comparison of mechanism and functional effects of magnesium and statin pharmaceuticals." J. Am. Coll. Nutr. 23(5):501S-5S, 2004.
"Statin-induced myopathy: minimize the risk and manage according to symptoms and creatine kinase levels." Drugs Ther. Perspect. 26(10):21-23, 2010.
Tomaszewski et al., "Statin-induced myopathies." Pharmacological Reports 63:859-66, 2011.
Wilkinson et al., "Effects of leucine and its metabolite beta-hydroxy-beta-methylbutyrate on human skeletal muscle protein metabolism." J. Physiol. 591(11):2911-23, 2013.
Wilson et al., "Effects of beta-hydroxy-beta-methylbutyrate (HMB) on exercise performance and body composition across varying levels of age, sex, and training experience: A review." Nutrition & Metabolism 5:1, 2008.
Wilson et al., "Beta-hydroxy-beta-methylbutyrate free acid reduces markers of exercise-induced muscle damage and improves recovery in resistance-trained men." British Journal of Nutrition 110:538-44, 2013.

* cited by examiner

*Primary Examiner* — My-Chau T Tran
(74) *Attorney, Agent, or Firm* — McDonnell Boehnen Hulbert & Berghoff LLP

(57) ABSTRACT

Disclosed herein are methods and compositions for alleviating side effects of statin administration, such as myopathic or myalgic side effects, short-term memory loss, abnormal liver function, glucose intolerance, hyperglycemia, increased risk for diabetes, or cumulative trauma disorder, comprising administration of β-hydroxy β-methylbutyrate (HMB) to an individual taking a statin. Also disclosed are methods and compositions for alleviating acute rhabdomyolysis comprising administration of HMB. The disclosure further provides uses of HMB in combination with a statin to alleviate side effects of statin administration.

25 Claims, 5 Drawing Sheets

METHODS FOR ALLEVIATING STATIN MYOPATHY

CROSS-REFERENCE TO RELATED APPLICATIONS

This application is a continuation of International Application No. PCT/US2015/023102, filed Mar. 27, 2015, which claims the benefit of U.S. Provisional Application No. 61/971,072, filed Mar. 27, 2014, the disclosures of both of which are incorporated by reference herein in their entireties.

BACKGROUND OF THE INVENTION

HMG-CoA reductase inhibitors, commonly known as statins, are a class of drugs used to lower cholesterol levels by inhibiting the enzyme HMG-CoA reductase, which catalyzes the rate-limiting conversion of HMG-CoA into mevalonate by HMG-CoA reductase during de novo cholesterol biosynthesis. Statins are used primarily to treat hyperlipidemias and are the most effective lipid-lowering drugs currently available. They have also been shown to exhibit pleiotropic effects and may have potential uses in the treatment of other conditions, such as diabetes, depression, cancer, osteoporosis, ventricular arrhythmias, peripheral arterial disease, and idiopathic dilated cardiomyopathy.

Side effects of statins include myopathy (including myalgia), increased risk of diabetes, short-term memory loss, cumulative trauma disorder, and abnormalities in liver enzyme tests. Myopathy is the most common side effect, with symptoms that can include muscle fatigue, weakness, pain, and rhabdomyolysis (i.e., the breakdown of muscle fibers that leads to the release of muscle fiber contents (inter alia, myoglobin) into the bloodstream). Rhabdomyolysis is rare, occurring in ~0.1% of patients; the occurrence of other myopathic symptoms has been estimated at 1-5% of patients in controlled studies using selected patients with 35% of eligible patients excluded (LaRosa et al., *New England Journal of Medicine* 2005, 352: 1425-35). An observational study (PRIMO) involving 7924 French unselected outpatients on statin therapy, reported 10.5% of statin users experienced statin-related myalgia/myopathy (Bruckert et al., *Cardiovascular Drugs and Therapy* 2005, 19: 403-14). Other observational studies have estimated that 9-20% of statin users experience statin-related muscle symptoms. Physical exercise appears to exacerbate the incidence of myalgia, with as many as 25% of statin users who exercise experiencing muscle fatigue, weakness, aches, and cramping.

Thus, there is a need in the art to improve treatment of statin-related diseases and disorders by alleviating said deleterious side effects.

SUMMARY OF THE INVENTION

This disclosure provides certain advantages and advancements over the prior art, in particular, methods for alleviating statin-induced myopathy and/or myalgia (SIM) comprising administering β-hydroxy β-methylbutyrate (HMB) to an individual taking a statin. In alternative embodiments, the disclosure provides methods for alleviating myopathy and/or myalgia, such as acute rhabdomyolysis, in individuals not taking a statin comprising administering HMB.

In one aspect, the disclosure provides methods for alleviating one or more side effects of statin administration, comprising supplementing statin administration with administration of a therapeutically effective amount of β-hydroxy β-methylbutyrate (HMB). In some embodiments, the one or more side effects of statin administration are any one or a plurality of myopathic or myalgic side effects, short-term memory loss, abnormal liver function, glucose intolerance, hyperglycemia, increased risk for diabetes, or cumulative trauma disorder. In some embodiments, HMB is administered at a dosage of approximately 1 to 6 grams/day, or otherwise at a dosage of approximately 2 to 4 grams/day. In some embodiments, HMB is administered at a dosage of approximately 3.0 grams/day. In some embodiments, HMB is administered at a dosage of approximately 2 grams taken twice a day. In particular embodiments, the invention provides pharmaceutical formulations of HMB comprising a therapeutically effective amount thereof and pharmaceutically acceptable excipients, diluents, or other formulating agents. In some embodiments, the statin is atorvastatin, cerivastatin, fluvastatin, lovastatin, mevastatin, pitavastatin, pravastatin, rosuvastatin, or simvastatin. In some embodiments, the statin is rosuvastatin.

In another aspect, the disclosure provides methods for alleviating acute rhabdomyolysis, comprising administering a therapeutically effective amount of β-hydroxy β-methylbutyrate (HMB).

In another aspect, the disclosure provides pharmaceutical formulations comprising a statin and a myopathic or myalgic statin side effect-alleviating amount of β-hydroxy β-methylbutyrate (HMB). In some embodiments, the statin is atorvastatin, cerivastatin, fluvastatin, lovastatin, mevastatin, pitavastatin, pravastatin, rosuvastatin, or simvastatin. In some embodiments, the statin is rosuvastatin.

In another aspect, the disclosure provides uses of HMB in combination with a statin to alleviate one or more side effects of statin administration. In some embodiments, the one or more side effects of statin administration are myopathic or myalgic side effects, short-term memory loss, elevated alanine transaminase (ALT) or aspartate transaminase (AST) levels, glucose intolerance, hyperglycemia, increased risk for diabetes, or cumulative trauma disorder. In some embodiments, the statin is atorvastatin, cerivastatin, fluvastatin, lovastatin, mevastatin, pitavastatin, pravastatin, rosuvastatin, or simvastatin.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, in which.

Figure 1:
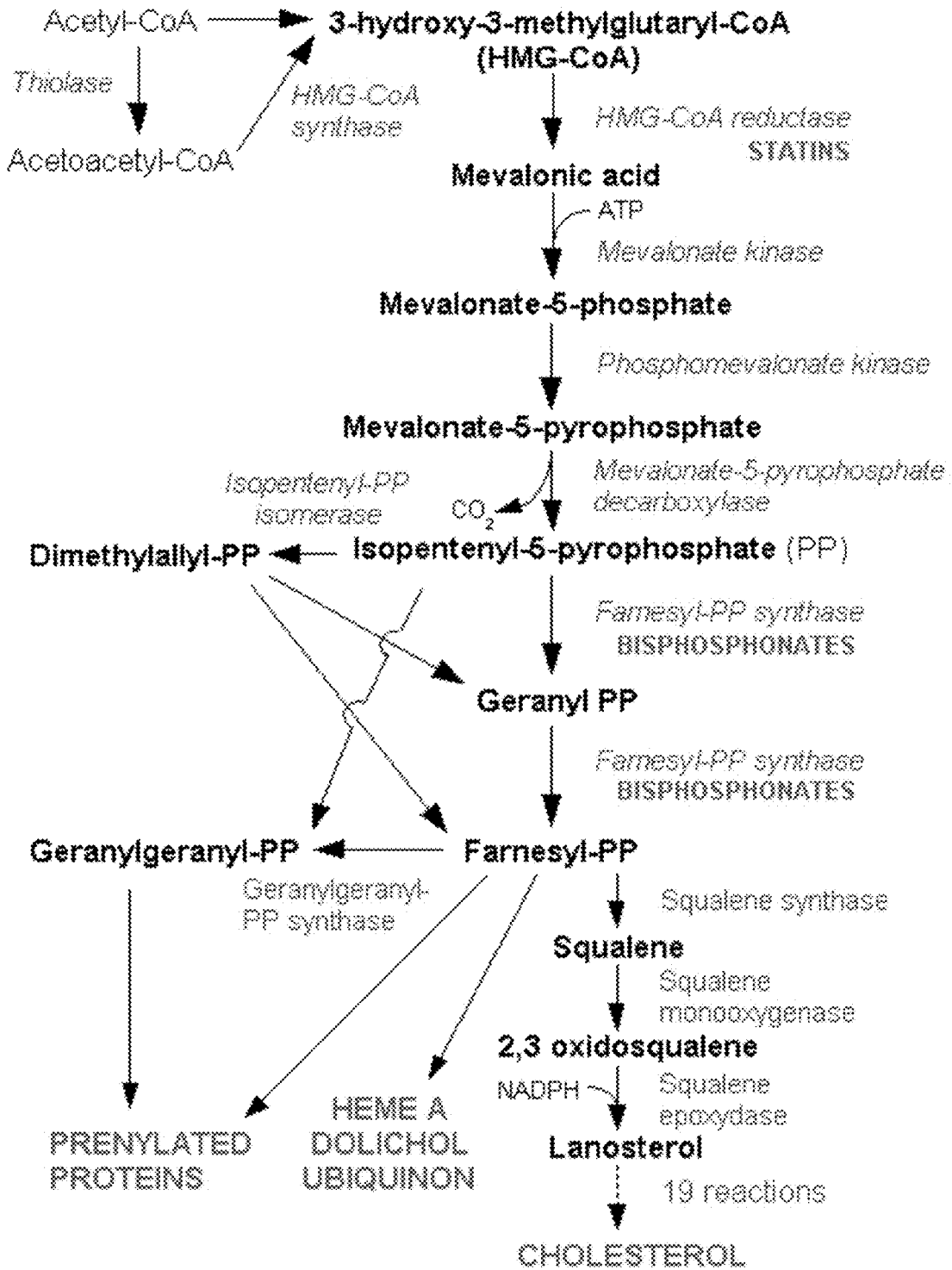
FIG. 1 is a schematic of the human cholesterol biosynthesis pathway. Statins inhibit the initial step (conversion of HMG-CoA to mevalonic acid by HMG-CoA reductase), thereby preventing the downstream metabolic cascade. HMB reverses this inhibition, allowing isoprenoid production, the ubiquinone pathway and on-site myocyte cholesterol synthesis to proceed.
Figure 2:
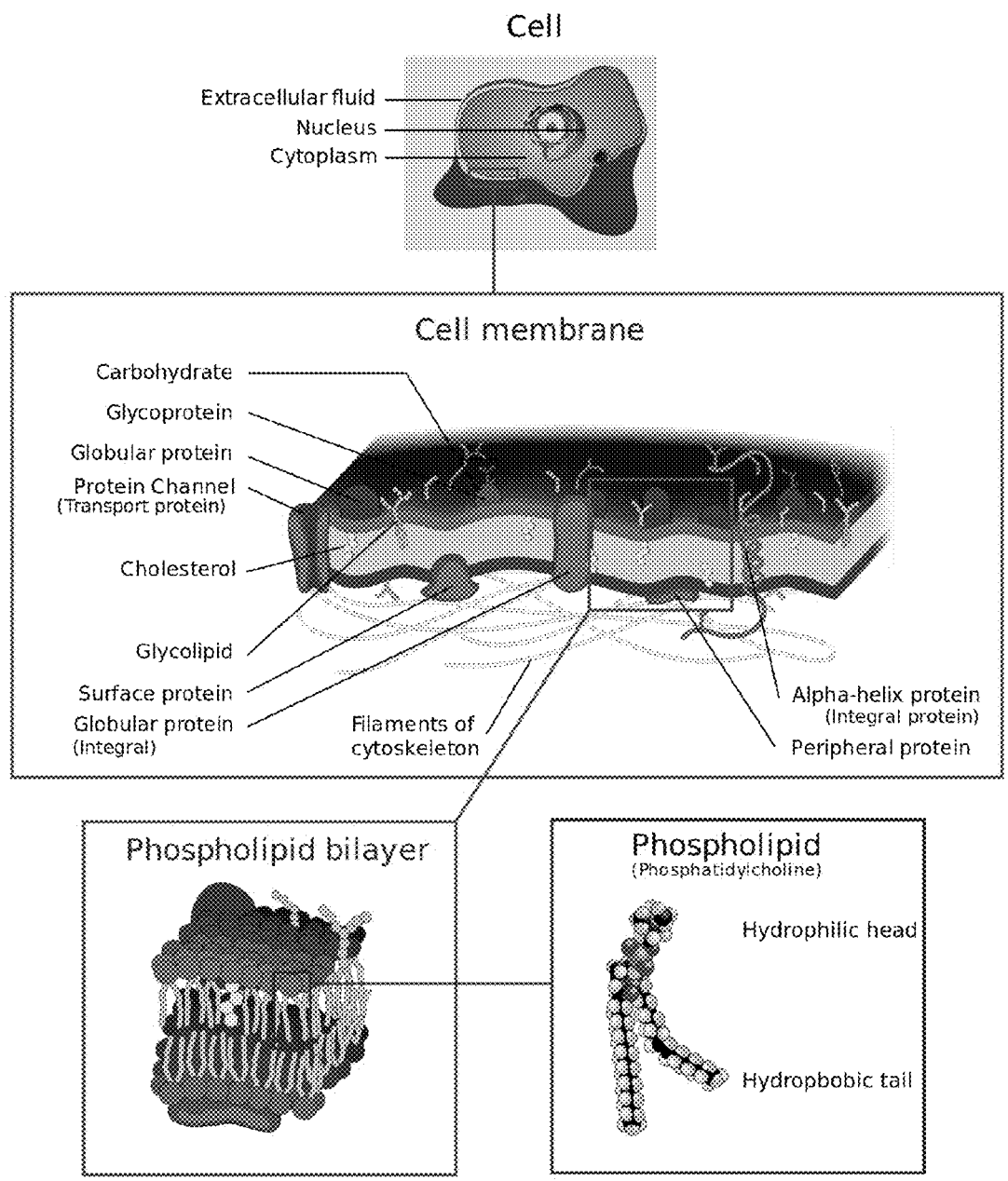
FIG. 2 shows the structure of a mammalian cell membrane. Cholesterol is an integral cell membrane component and is synthesized in situ to maintain cellular structural integrity, particularly in myocytes. In situ cholesterol biosynthesis is a process inhibited by statins but promoted by HMB.

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the present invention.

DETAILED DESCRIPTION OF THE INVENTION

All publications, patents and patent applications cited herein are hereby expressly incorporated by reference for all purposes.

Before describing the present invention in detail, a number of terms will be defined. As used herein, the singular forms "a", "an", and "the" include plural referents unless the context clearly dictates otherwise. For example, reference to a "protein" means one or more proteins.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the term "statin" refers to a 3-hydroxy-3-methylglutaryl coenzyme A (HMG-CoA) reductase inhibitor. Statins block the rate-limiting step in de novo cholesterol biosynthesis, namely, the conversion of HMG-CoA into mevalonate by HMG-CoA reductase. Statins are used primarily as cholesterol-lowering (specifically, low-density lipoprotein (LDL)-lowering) medications to treat hyperlipidemias, such as hypercholesterolemia. Examples of statins with brand names and typical daily adult dose ranges provided in parentheses include: atorvastatin (LIPITOR®) (10-80 mg), fluvastatin (LESCOL®) (20-80 mg), lovastatin (MEVACOR®) (10-80 mg), pitavastatin (LIVALO®) (1-4 mg), pravastatin (PRAVACHOL®) (10-80 mg), rosuvastatin (CRESTOR®) (5-20 mg), and simvastatin (ZOCOR®) (5-80 mg).

The following disclosure is provided without being limited to any mechanism and solely to explicate what is understood in the art regarding statin-mediated decrease in circulating LDL. LDL-B (apo-lipoprotein B) is a lipid carrier molecule, manufactured in the liver, that is highly atherogenic. LDL-B levels are regulated by liver LDL receptors that bind to circulating LDL particles, resulting in their absorption and ultimate destruction in liver. The greater the density of LDL receptor sites on liver cell (hepatocyte) surfaces, the lower the level of LDL-B cholesterol in circulation. PCSK9 (proprotein convertase subtilisin/kexin type 9) is a glycoprotein expressed by the liver that degrades LDL receptors. When this occurs, LDL-B levels rise in circulation. Statins, by inhibiting HMG CoA reductase, reduce intra-cellular cholesterol production in the hepatocyte, in turn activating SREBP-2 (sterol regulatory element binding protein-2). This pathway then upregulates hepatic LDL receptor sites, increasing liver clearance of circulatory LDL-B. Although statins also upregulate PCSK9 levels by 7%, this increase is more than offset by the upregulation of SREBP-2, resulting in a net decrease in LDL B particles in solution.

Statins also exert an effect on myocytes (skeletal muscle cells) by interfering with intra-cellular cholesterol synthesis, an activity that has no relationship to circulating LDL-B levels. HMB is a metabolite of an essential amino acid (branch chain amino acid leucine), and while it is taken up by myocytes it is not stored in hepatocytes. For this reason, HMB can unexpectedly be used concurrently with statin agents without subverting the hepatic effect of statins in lowering LDL-B cholesterol.

As used herein, the terms "side effect," "peripheral effect," and "secondary effect" are interchangeable and refer to effects or symptoms caused by a drug, medication, or pharmaceutical other than its primary, intended effect or indication.

As used herein, the terms "myopathy" and "myopathic" refer to muscle damage, dysfunction, or disease wherein muscle fibers do not function properly for any one of many reasons, resulting in, for example, muscle weakness, muscle cramps, muscle spasms, muscle stiffness, or elevation of creatine kinase (CK or CPK) levels in blood. For example, myositis may be assessed when CK levels rise above a certain amount, such as above a 1 to 10-fold "upper limit of normal" (ULN). In some cases, muscle symptoms might be observed without a concomitant elevation in CK levels. In other cases, CK levels might be elevated without muscle symptoms.

As used herein, the term "rhabdomyolysis" refers to a type of myopathy involving the release of muscle cell products into the bloodstream following muscle cell damage. Some of these muscle cell products, such as myoglobin, are harmful to the kidneys and may lead to kidney damage or kidney failure. Rhabdomyolysis can also result in disseminated intravascular coagulation and/or death. Rhabdomyolysis might be defined, for example, by CK levels above 10,000 IU/liter or above a 10-fold ULN with an elevation in serum creatinine or a need for hydration therapy. Rhabdomyolysis may be statin-induced or non-statin-induced. For example, in some cases rhabdomyolysis is induced by intense exercise. In some embodiments of the methods disclosed herein, HMB administration is used to treat rhabdomyolysis induced by statin administration. In some embodiments, HMB administration is used to treat non-statin-induced rhabdomyolysis.

As used herein, the terms "myalgia" and "myalgic" refer to muscle pain, which may be a symptom of many diseases and disorders, including myopathy.

Myopathy and/or myalgia are the most common side effects associated with the use of statins. Symptoms of statin-induced myopathy include any combination of muscle pain, muscle weakness, or muscle tenderness, such as an aching or cramping sensation in muscles. Tendon pain and nocturnal leg cramping are other possible symptoms. Statin-induced myopathies are typically exacerbated by exercise; thus, athletes are frequently particularly intolerant to statin therapy.

The incidence of statin-induced myopathy or myotoxicity is estimated as about 1.5-5% in randomized-control clinical trials.

The pathology of statin-induced myopathy is not fully understood, particularly because multiple pathophysiological mechanisms may contribute to statin myotoxicity. Without being limited to these or any other explanations of how the invention may work or the biochemical or physiological mechanisms or explanations thereof, these mechanisms include statin-induced alterations in muscular membrane composition, isoprenoid and ubiquinone synthesis, mitochondrial function, calcium homeostasis, rate of apoptosis, and atrogin-1 induction.

Figure 3A:
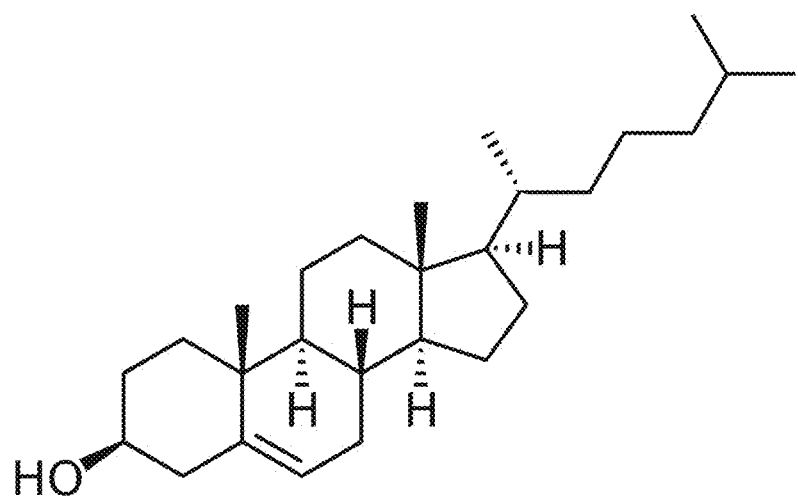
FIG. 3A shows the chemical structure of cholesterol.
Figure 3B:
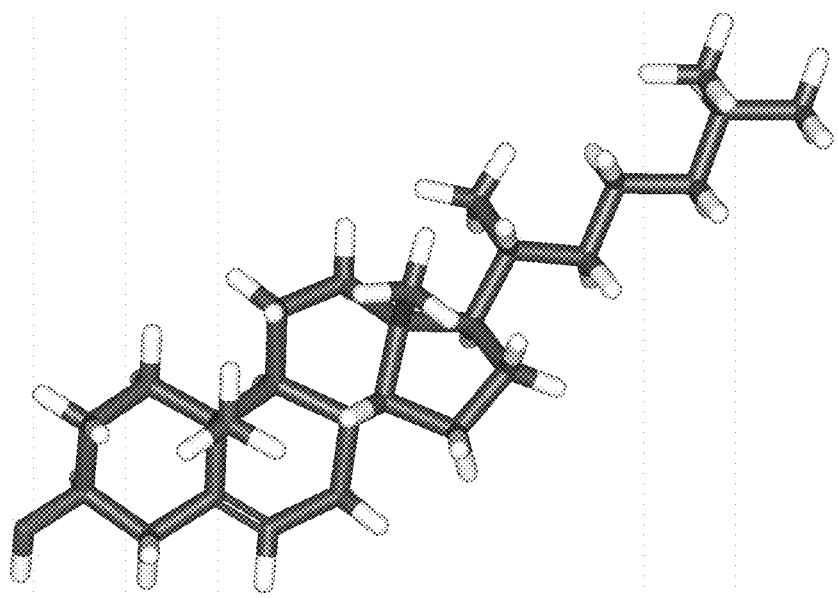
FIG. 3B shows a molecular stick model of cholesterol.
Figure 4:
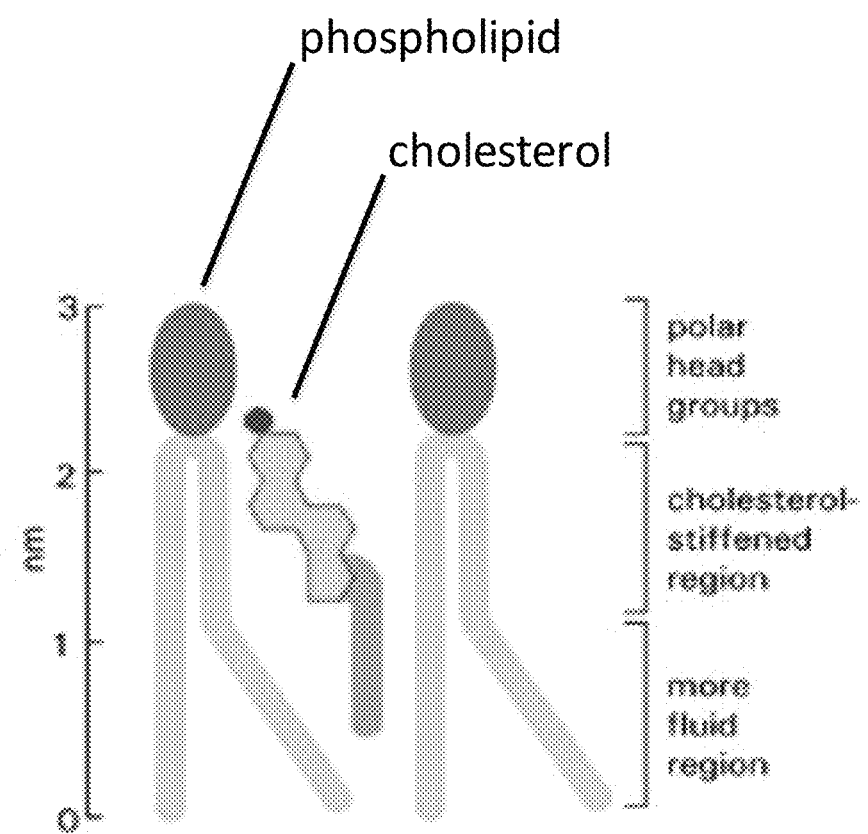
FIG. 4 depicts a molecule of cholesterol between two phospholipid molecules within a lipid bilayer.

The lipid bilayer of many cell membranes consists not only of phospholipids, but also cholesterol and glycolipids. Eukaryotic plasma membranes contain especially large amounts of cholesterol—up to one cholesterol molecule for every phospholipid molecule. Cholesterol is thus an integral cell membrane component. Cholesterol molecules enhance the permeability-barrier properties of the lipid bilayer and modulate the fluidity of cell membranes, including the membranes of muscle cells. Membrane-bound cholesterol molecules orient themselves in the bilayer with their hydroxyl groups (FIGS. 3A and 3B) toward the polar head groups of the phospholipid molecules (FIG. 4). In this position, cholesterol's rigid, plate-like steroid rings interact with—and partly immobilize—those regions of the phospholipid hydrocarbon chains closest to the polar head groups. By decreasing the mobility of the first few $CH_2$ groups of the phospholipid hydrocarbon chains, cholesterol makes the lipid bilayer less deformable in this region and thereby decreases the permeability of the bilayer to small water-soluble molecules. Although cholesterol tends to make lipid bilayers less fluid at the high concentrations found in most eukaryotic plasma membranes, it also prevents component hydrocarbon chains from coming together and crystallizing. In this way, it inhibits possible phase transitions. Because statins interfere with cholesterol biosynthesis, they also affect myocyte membrane fluidity. Alterations in membrane fluidity in turn can affect membrane ion channel function, which plays an integral role in membrane excitability. For example, chloride channels in skeletal muscle membranes control resting membrane potential and membrane repolarization. Thus, statin-induced depletion of cholesterol likely disturbs muscle cell function.

According to the isoprenoid synthesis mechanism, statins may cause myopathy by inhibiting synthesis of isoprenoids, for which mevalonate is a precursor. Statin-induced depletion of isoprenoids may in turn disturb cellular respiration, causing myopathy. Under the calcium homeostatis theory of statin-induced myopathy, statin-mediated depletion of isoprenoids leads to decreased inhibition of calcium ion ($Ca^{2+}$) channels in muscle cells, which results in impaired calcium ion homeostasis and impaired myocyte function. Other possible mechanisms of statin-induced myopathy are related to statins' "pleiotropic effects," which are cholesterol-independent effects of statins. These pleiotropic effects include statin-mediated improvement in endothelial function, stabilization of atherosclerotic plaques, decreases in oxidative stress and inflammation, and inhibition of thrombogenic responses. However, statins can also trigger skeletal muscle apoptosis (i.e. programmed cell death) and, thus, myopathy. Statin-induced myopathy may also be caused through induction, by any statin, of atrogin-1, a human gene that induces muscle pathology directly and is activated by inhibition of the geranasylgeranasyl isoprenoid pathway, part of the cholesterol synthesis cascade obstructed by statins. (See Cao et al., 2009, *FASEB J.* 23(9):2844-54.)

Statin myopathy appears only in a subset of muscle fibers. In general, the human body consists of a 1:1 ratio of Type 1 (aerobic, slow-twitch) muscle fibers and Type 2 (anaerobic, fast-twitch) muscle fibers. All muscle fibers require cholesterol for cellular repair. Type 2 fibers express LDL receptors, which enable absorption of circulating cholesterol (see Takeda et al., *Pathobiology*, 2014, 81:94-99). Type 1 fibers, which are used in ordinary activities such as standing and walking, lack LDL receptors and are thus dependent on intracellular cholesterol synthesis, a process inhibited by statin agents. The resulting deficit in cellular cholesterol in Type 1 fibers can lead to statin myopathy.

As used herein, the terms "HMB," "β-hydroxy β-methylbutyric acid," "β-hydroxy β-methylbutyrate," "3-hydroxy-3-methylbutanoic acid," "3-hydroxy 3-methyl butyrate," "β-hydroxyisovaleric acid," and "3-hydroxyisovaleric acid" are interchangeable and refer to the compound of formula (I):

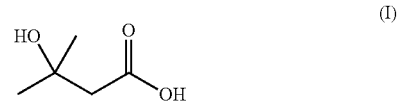

(I)

HMB is a metabolite of the amino acid leucine and is synthesized in the human body, where it is converted into the cholesterol precursor HMG-CoA. HMB is used as a dietary supplement by athletes and bodybuilders to enhance performance and training. Daily doses of HMB as a dietary supplement range from about 2 to 5 grams per day, more commonly about 3 grams per day. In terms of dose per body mass, daily doses of HMB as a dietary supplement range from about 17 mg/kg body weight to about 38 mg/kg body weight. Daily HMB dietary supplement dosages can be divided up into, for example, one to four administrations per day.

Figure 5:
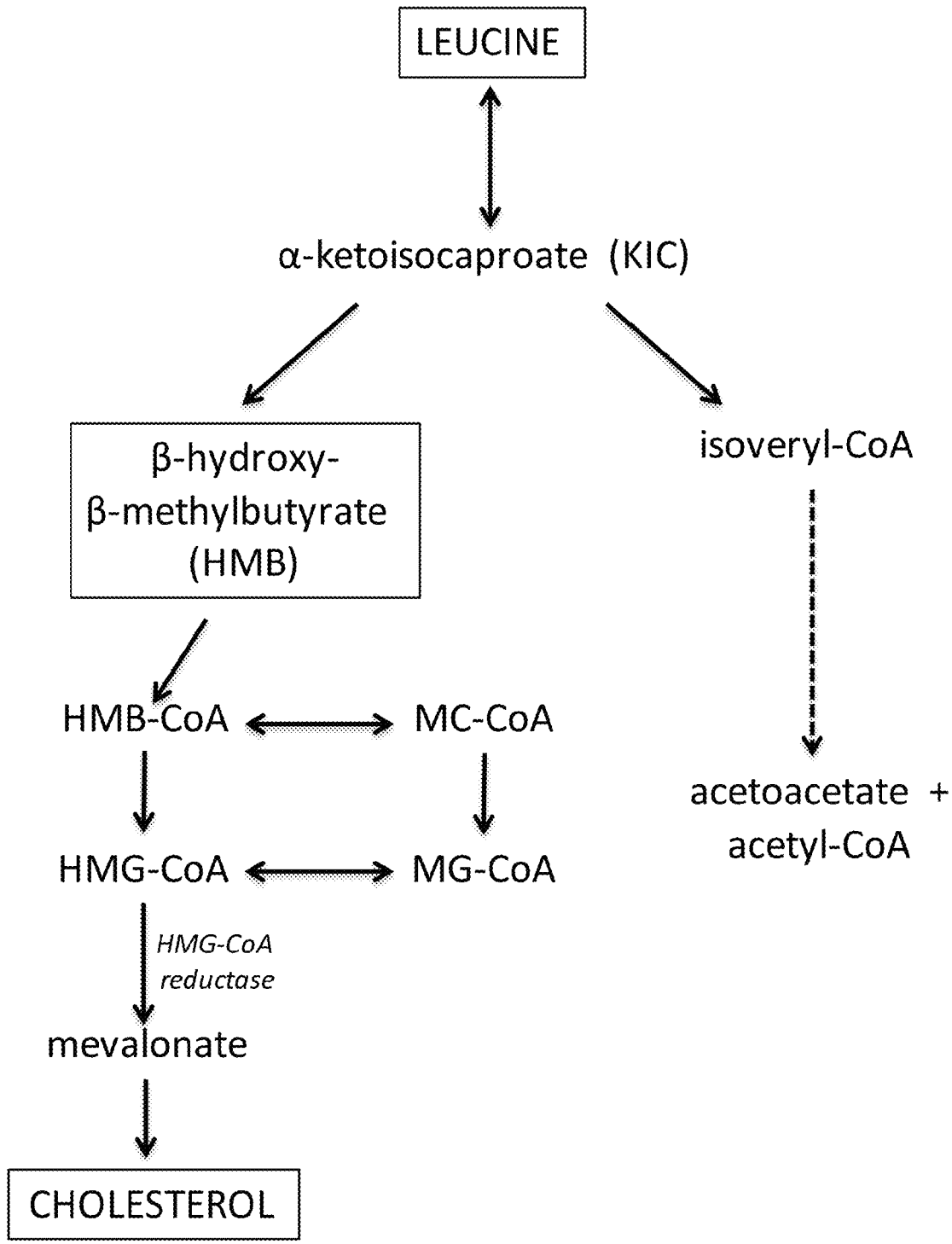
FIG. 5 is a schematic of some elements of leucine, α-ketoisocaproate (KIC), and HMB metabolism in mammals, which comprises an alternative pathway in the myocyte for production of HMG CoA. HMB is converted to HMB-CoA, then to β-hydroxy-β-methylglutaryl-CoA (HMG-CoA), the conversion of which into mevalonate is catalyzed by HMG-CoA reductase. Mevalonate is eventually converted into cholesterol, as shown in FIG. 1. MC-CoA refers to β-methylcrotonyl-CoA; MG-CoA refers to β-methyl-gluconyl-CoA.

The role of HMB in metabolism of leucine into cholesterol is shown in FIG. 5. It takes about 60 grams of leucine to produce 1 gram of HMB; therefore, leucine supplements are ineffective as a source of HMB.

Toxicologically, the "No Observed Adverse Effect Level" (NOAEL; the highest dose not associated with any toxic signs) for HMB oral ingestion in rats is 3490 mg/kg for male rats and 4160 mg/kg for female rats (see Baxter et al., *Chem Toxicol.*, 2005, 43(12):1731-41). This is an estimated human equivalent of 558 mg/kg and 665 mg/kg for men and women, respectively; assuming a body weight of 150 lbs equates to 38 g (males) and 45 g (females). Human toxicological studies have shown that approximately 6 g HMB daily (78 mg/kg) for one month in untrained young males subject to exercise did not show any toxic effects on serum parameters (half the dose had a spontaneous increase in basophils, considered to be insignificant) and 3 g of HMB daily for up to 8 weeks in both youth and older persons has similarly failed to alter toxicological parameters in serum. This dose has been shown to be safe for one year of administration (see Gallagher et al., *Med Sci Sports Exerc.*, 2000 December; 32(12):2116-19; Nissen et al., *J Nutr.*, 2000 August; 130(8):1937-45). Overall, standard doses of HMB appear to be well-tolerated over long periods of time.

As the person of ordinary skill in the art will appreciate, HMB can be provided as an HMB derivative or prodrug, depending, e.g., on the desired end properties of the compositions and methods. For example, HMB may be modified with a suitable prodrug group that metabolizes or otherwise transforms under conditions of use to yield HMB. In one embodiment, HMB may be modified at the carboxylic acid moiety with a suitable group that can be hydrolyzed. In these embodiments, HMB is provided for example as an ester or a lactone. Suitable HMB esters include, but are not limited to, methyl ester, ethyl ester, and isopropyl ester. Exemplary, non-limiting HMB lactone includes isovalaryl lactone. HMB may also be modified at the hydroxy moiety, for example, with an acetate group. HMB derivatives to be used for the compositions and methods of the present disclosure are within the skill of the person skilled in the art using routine trial and experimentation. In some embodiments, HMB derivatives or pro-drugs are used in the compositions and methods disclosed herein in order to provide delayed or sustained release of HMB.

As used herein, the term "hydrate" refers to a compound that is complexed with at least one water molecule. For example, HMB monohydrate refers to a molecule of HMB complexed with one water molecule.

As used herein, the term "alleviate" refers to the amelioration or lessening of the severity of a side effect or symptom or substantially eliminating said side effect or symptom.

As used herein, the term "administer" or "administration" refers to oral ("po") administration, administration as a suppository, topical contact, intravenous ("iv"), intraperitoneal ("ip"), intramuscular ("im"), intralesional, intranasal or subcutaneous ("sc") administration, or the implantation of a slow-release device e.g., a mini-osmotic pump, to an individual. Administration can be by any route including parenteral and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and equivalent methods and modalities know to those of skill in the art.

As used herein, the term "co-administer" refers to administering more than one pharmaceutical agent to a patient. In some embodiments, co-administered pharmaceutical agents are administered together in a single dosage unit. In some embodiments, co-administered pharmaceutical agents are administered separately. In some embodiments, co-administered pharmaceutical agents are administered at the same time. In some embodiments, co-administered pharmaceutical agents are administered at different times.

The term "pharmaceutical formulation" refers to a preparation which is in such form as to permit a biological activity of an active ingredient to be effective, and which contains no additional components which are unacceptably toxic to a subject to which the formulation would be administered.

As used herein, the terms "extended release," "sustained release," or "controlled release" refer to compositions that are characterized by having at least one active component having a release profile over an extended period of time, in contrast to "immediate release" pharmaceutical formulations. In some embodiments, the compositions disclosed herein release their active components over a period of about 6 hours to about 72 hours, or about 12 hours to about 48 hours, or about 12 hours to about 36 hours, or about 18 hours to about 30 hours, or about 24 hours. In some embodiments, the active component is released over a time period such that the composition can be administered to a subject once a day, for example, over 24 hours.

In some embodiments, the active ingredients of the compositions and methods disclosed herein are formulated in free acid or free base form. For example, in some embodiments, HMB is formulated as HMB free acid. In some embodiments, HMB free acid is administered orally or sublingually as a gel.

In some embodiments, the active ingredients of the compositions and methods disclosed herein are formulated as a pharmaceutically acceptable salt. As used herein, the term "pharmaceutically acceptable salt" refers to salts of the compounds of the present invention derived from the combination of such compounds and a pharmaceutically acceptable organic or inorganic acid (acid addition salts) or a pharmaceutically acceptable organic or inorganic base (base addition salts) which retain the biological effectiveness and properties of the compounds of the present invention and which are not biologically or otherwise undesirable. Examples of pharmaceutically acceptable salts include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002. The compounds of the present invention may be used in either the free base or salt forms, with both forms being considered as being within the scope of the present invention. For example, HMB may be administered as a salt selected from the group consisting of a sodium salt, a potassium salt, a magnesium salt, a chromium salt, and a calcium salt. Other non-toxic salts, such as other alkali metal or alkaline earth metal salts can be used. In some embodiments, HMB may be administered as calcium HMB monohydrate. Other salts which may act as carriers include succinate, fumarate and medoximil.

Extended release salts such as succinate may be bound to HMB such that the HMB is released at a controlled rate. In some embodiments, HMB is released at a rate such that the HMB can be administered once a day. HMB has a relatively short half-life and reaches peak levels quickly. Therefore, binding HMB to a slow release carrier may have some utility in terms of compliance and efficacy.

HMB may be combined with any of the above-mentioned statins to provide combination lipid lowering therapy in patients who are otherwise statin intolerant. Examples would include HMB/atorvastatin, HMB/rosuvastatin, HMB/pravastatin, HMB/simvastatin and HMB/lovastatin.

In one aspect, the disclosure provides methods for alleviating one or more side effects of statin administration, the method comprising supplementing statin administration with administration of a therapeutically effective amount of β-hydroxy β-methylbutyrate (HMB), wherein one or more side effects of statin administration are alleviated. In some embodiments, the one or more side effects of statin administration are one or a plurality of myopathic or myalgic side effects, short-term memory loss, abnormal liver function, glucose intolerance, hyperglycemia, increased risk for diabetes, or cumulative trauma disorder. In some embodiments, the myopathic or myalgic side effects include muscle fatigue, muscle weakness, muscle pain, and/or rhabdomyolysis. In some embodiments, the rhabdomyolysis is acute rhabdomyolysis.

As used herein, the phrase "abnormal liver function" refers to liver function characterized by elevated liver functions tests (LFTs), and in particular, elevations in levels of alanine transaminase (ALT, also known as SGPT) and/or aspartate transaminase (AST, also known as SGOT) enzymes. Elevated ALT and AST levels are indicators of liver damage. Other terms for this condition include transaminasemia and transaminitis. LFTs are "elevated" when above the normal ranges, which are about 8-40 U/L for ALT and AST.

As used herein, the phrase "glucose intolerance" refers to a metabolic condition resulting in higher-than-normal levels of blood glucose. Glucose intolerance can include type 1, type 1.5, and type 2 diabetes. Measurement of glycated hemoglobin levels (hemoglobin A1c or HbA1c) in a patient is one way to assess glucose intolerance and/or diabetes. For people without diabetes, the normal range for the hemoglobin A1c test is between 4% and 5.6%. Hemoglobin A1c levels between 5.7% and 6.4% indicate increased risk of diabetes, and levels of 6.5% or higher indicate diabetes. Thus, in some embodiments of the methods disclosed herein, glucose intolerance is characterized by hemoglobin A1c levels at or exceeding about 5.6%, or about 5.7%, or about 6.4%, or about 6.5%.

In some embodiments of the methods disclosed herein, the HMB is administered at a dosage of about 0.5 to about 10 grams/day, or of about 1.0 to about 6.0 grams/day, or of about 2.0 to 4.0 grams/day. In some embodiments, the HMB is administered at a dosage of approximately 4 grams/day. In some embodiments, the HMB is administered at a dosage of approximately 3 grams/day. In some embodiments, the HMB is administered 1 to 5 times per day. In some embodiments, the HMB is administered 3 times per day. In some embodiments, the HMB is administered 2 times per day. In some embodiments, the HMB is administered 1 time per day.

In some embodiments, HMB is administered as a calcium salt, such as calcium HMB monohydrate. In some embodiments, HMB is administered as HMB free acid.

In some embodiments of the methods disclosed herein, HMB is administered in an extended-release form. In some embodiments, the extended-release form of HMB comprises succinate in order to extend release time in the gastrointestinal tract. In some embodiments, extended-release forms of HMB are designed or formulated to be administered one to three times per day. In some embodiments, extended-release forms of HMB are formulated to be administered once per day.

In some embodiments of the methods disclosed herein, the statin is atorvastatin, cerivastatin, fluvastatin, lovastatin, mevastatin, pitavastatin, pravastatin, rosuvastatin, or simvastatin. In some embodiments, the statin is rosuvastatin.

In another aspect, the disclosure provides methods for treating acute rhabdomyolysis comprising administering a therapeutically effective amount of HMB. In some embodiments, the acute rhabdomyolysis is not statin-induced. For example, acute rhabdomyolysis is caused by dehydration, trauma, and/or intense exercise. In some embodiments, HMB is administered at a dosage of from about 3 grams/day to about 15 grams/day. In some embodiments, HMB is administered at a dosage of about 12 grams/day. In some embodiments, HMB is administered at a dosage of 6 grams twice a day. In some embodiments, HMB is HMB free acid. In some embodiments, HMB is administered for at least three days.

In another aspect, the disclosure provides pharmaceutical formulations comprising a statin and a myopathic or myalgic statin side effect-alleviating amount of β-hydroxy β-methylbutyrate (HMB). In some embodiments of the pharmaceutical formulations disclosed herein, the myopathic or myalgic statin side effect-alleviating amount of HMB comprises a dosage of HMB of about 0.5 to about 10 grams/day, or of about 1.0 to about 6.0 grams/day, or of about 2.0 to 4.0 grams/day. In some embodiments, myopathic or myalgic statin side effect-alleviating amount of HMB comprises a dosage of approximately 3.0 grams/day. In some embodiments, the HMB is HMB monohydrate. In some embodiments, the HMB is HMB calcium salt.

In some embodiments of the pharmaceutical formulations disclosed herein, the statin is atorvastatin, cerivastatin, fluvastatin, lovastatin, mevastatin, pitavastatin, pravastatin, rosuvastatin, or simvastatin. In some embodiments, the statin is rosuvastatin. In some embodiments, the ratio of statin to HMB is approximately 0.001 to 0.1 by weight. In some embodiments, the ratio of statin to HMB is about 0.008, or about 0.01, or about 0.02, or about 0.03, or about 0.04, or about 0.05, or about 0.06, or about 0.07, or about 0.08, or about 0.09 by weight. In some embodiments, the ratio of statin to HMB is approximately 0.01 by weight. In some embodiments, the amount of HMB is from about 1.0 gram to about 4.0 grams.

In some embodiments of the pharmaceutical formulations disclosed herein, HMB is formulated for extended release. In some embodiments, extended-release forms of HMB comprise succinate in order to extend release time in the gastrointestinal tract. In some embodiments, extended-release forms of HMB are designed or formulated to be administered one to three times per day. In some embodiments, extended-release forms of HMB are formulated to be administered once per day.

In another aspect, the disclosure provides uses of HMB in combination with a statin to alleviate one or more side effects of statin administration. In some embodiments, the one or more side effects of statin administration are one or a plurality of myopathic or myalgic side effects, short-term memory loss, abnormal liver function, glucose intolerance, hyperglycemia, increased risk for diabetes, or cumulative trauma disorder. In some embodiments, the myopathic or myalgic side effects include muscle fatigue, muscle weakness, muscle pain, and/or rhabdomyolysis. In some embodiments, the rhabdomyolysis is acute rhabdomyolysis.

In some embodiments of the uses disclosed herein, the HMB is administered at a dosage of about 0.5 to about 15 grams/day, or of about 1.0 to about 6.0 grams/day, or of about 2.0 to 4.0 grams/day. In some embodiments, the HMB is administered at a dosage of approximately 4 grams/day. In some embodiments, the HMB is administered at a dosage of approximately 3 grams/day. In other embodiments, the HMB is administered at a dosage of about 3.0 to about 15.0 grams/day. In some embodiments, the HMB is administered at a dosage of about 12.0 grams/day. In some embodiments, the HMB is administered 1 to 5 times per day. In some embodiments, the HMB is administered 3 times per day. In some embodiments, the HMB is administered 2 times per day. In some embodiments, the HMB is administered 1 time per day. In some embodiments, HMB is administered as a calcium salt, such as calcium HMB monohydrate. In some embodiments, HMB is administered as HMB free acid.

In some embodiments of the uses disclosed herein, HMB is administered in an extended-release form. In some embodiments, the extended-release form of HMB comprises succinate in order to extend release time in the gastrointestinal tract. In some embodiments, extended-release forms of HMB are designed or formulated to be administered one to three times per day. In some embodiments, extended-release forms of HMB are formulated to be administered once per day.

In some embodiments of the uses disclosed herein, the statin is atorvastatin, cerivastatin, fluvastatin, lovastatin, mevastatin, pitavastatin, pravastatin, rosuvastatin, or simvastatin. In some embodiments, the statin is rosuvastatin.

EXAMPLES

The Examples that follow are illustrative of specific embodiments of the invention, and various uses thereof. They are set forth for explanatory purposes only, and are not to be taken as limiting the invention.

Example 1

Initial Assessment of HMB Reversal of Statin Myalgia

A healthy, fully informed and consenting adult volunteer with severe rosuvastatin-induced myalgia and myopathy and pre-statin LDL of 260 was administered 1 gram HMB three times a day (3 grams/day total) while rosuvastatin therapy was continued. Within 72 hours of the initial HMB administration, statin myalgia/myopathy fully subsided. During brief intervals where HMB treatment was discontinued (i.e., unintentionally skipped doses), the subject reported a return of myalgia, which again subsided upon reinstatement of HMB treatment. An increase in HMB dosage to 6 grams/day provided no additional benefit.

Example 2

Clinical Study Evaluating the Effects of HMB Therapy on Patients with Statin-Induced Myopathy A clinical study was conducted to evaluate the effects of HMB on patients with statin-induced myopathy (SIM). A total of eighteen patients were evaluated for the study with informed written consent obtained. Of the eighteen patients, fourteen (14) ultimately qualified as having true statin myalgia and were enrolled in the study. All patients enrolled were under the care of a board certified cardiologist.

A summary of the enrolled patients and their outcomes is as follows:
1. All 14 had type 2a or mixed hyperlipidemia.
2. All 14 had been treated with multiple statin agents, in each case withdrawing from the statin agent due to myalgia/myopathy.
3. Of the 14 patients enrolled, 4 had elevated CPK's (creatine phosphokinase, a biomarker for myositis/rhabdomyolysis) secondary to SIM.
4. Five of the 14 patients had undergone prior percutaneous coronary intervention with stents.
5. One of the 14 patients had undergone prior coronary bypass surgery.
6. Four of the 14 patients had angiographically documented moderate coronary artery disease not requiring percutaneous coronary intervention (PCI)/coronary bypass.
7. Four of the 18 patients were disqualified due to the following:
   Patient's leg myalgia was secondary to angiographically proven peripheral vascular disease, not SIM and symptoms were consistent with this diagnosis.
   Patient's unilateral leg pain was secondary to neuropathy, not SIM.
   Patient complained of GI upset on combined statin+3-hydroxy 3-methylbutyrate and medication was discontinued. Of note, the patient's SIM-related myalgia resolved completely after HMB treatment.
   Patient presentation and clinical course were ultimately incompatible with statin myopathy.
8. All 14 qualified patients remained on combination statin (in some cases with Zetia to achieve target) plus HMB therapy after the initial duration of the study. As noted, of those who had previously discontinued statin therapy, all had been tried on multiple statin agents without success.
9. Follow up was conducted with all patients including out-patient visits and phone conversation.
10. All 14 qualifying patients responded to therapy with complete resolution of SIM symptoms.

Two available forms of HMB were utilized in this study: calcium monohydrate form as a powder and free acid (which is more bioavailable) form as a gel cap. The free acid form was used in one patient who experienced major CPK elevations (900-1000 IU/L range) and disabling myalgia on statins. The free acid form resulted in a significant decrease in CPK and resolution in symptoms with an improvement over the calcium monohydrate form (see summary for Patient D-4, below).

For this study, patients were evaluated using multiple laboratories with variable lab normal ranges, which are included. In the patient population as a whole, the full spectrum of SIM is presented, including statin myalgia without CPK elevation (myositis or rhabdomyolysis depending on severity), elevation of CPK without myalgia, post-statin elevation of CPK with and without pain, post-statin myalgia without CPK elevation, and, finally, statin-induced muscle weakness without myalgia. Also represented were other statin-induced side effects such as short-term memory loss and glucose intolerance.

Clinical summaries for patients enrolled in the study are provided below.

Patient A-1

53 year old female, diagnosed three years prior by her primary physician with severe hyperlipidemia, apparently mixed-type. She was otherwise in good health. Simvastatin was prescribed with resultant severe bilateral leg myopathy/myalgia. The patient's internist substituted Crestor® (rosuvastatin) for simvastatin with the hope of alleviating the patient's leg pain. The pain intensified and persisted, involving the quadriceps, gluteals, and pyriformis muscles bilaterally. She stopped Crestor® on her own accord but the pain abated only minimally and she was having difficulty walking. Six weeks after stopping Crestor®, still in pain, her CPK was elevated (242 IU/L, lab normal range 26-192) consistent with a persistent post-statin myositis. At that time, she was not physically active. She was placed on calcium HMB monohydrate, 2 g BID (twice daily) prior to re-introducing statin therapy. All pain completely resolved in 3 days. A repeat CPK was drawn 9 days later and was in normal range (87 IU/L, range 26-192). Subsequently, Crestor® at a dose of 10 mg daily was prescribed. The patient remained completely pain free after 3 months on statin therapy despite regularly exercising at the gym with a weights/cardio regimen. Subsequent lab results confirmed mixed rather than a pure type 2a hyperlipidemia, with triglycerides>400 mg %. Vascepa was added to her statin regimen along with a carbohydrate-restricted diet and regular exercise. Patient re-evaluation 3 months after beginning treatment with HMB: asymptomatic, no recurrence of leg, hip myalgia or biomarker (+) myositis on Crestor®, 10 mg daily +calcium HMB monohydrate 2 g BID. LDL=72 mg/dl. CPK=110 IU/L.

Patient B-2

60 year old male, with coronary heart disease, having undergone percutaneous coronary intervention with stent 10 years prior. Patient B-2 was statin intolerant and previous attempts on statin therapy had failed due to intractable leg myalgia. An alternative regimen of Welchol®, 6 tablets daily and Zetia®, 10 mg daily was prescribed with relief of myalgia. Prior to beginning HMB therapy, B-2 had elevated LDL=168 mg % on this combination non-statin therapy. Welchol® was discontinued and he was placed on Vytorin®, 10/40+calcium HMB monohydrate, 2 g BID. Repeat lab 50 days later demonstrated a drop in LDL to 110 mg % with a normal CPK (173 IU/L, lab normal range 44-196). Six months later, the patient remained compliant with his medication and remained completely asymptomatic on Vytorin®.

Patient C-3

Male, age 52, with medical problems that included type 2a hyperlipidemia, type 2 diabetes, hypertension and a benign mitral valve disorder. Multiple attempts at statin therapy on a variety of statins met with almost immediate failure due to statin intolerance in the form of myalgia, relieved only by discontinuing the statin. Zetia® as monotherapy was prescribed with modest success but he was unable to achieve clinical goals (<100 mg % LDL) for a diabetic patient. The patient was placed on Crestor®, 10 mg daily+calcium HMB monohydrate, 2 g BID. Three months later, he remained completely symptom free on statin therapy.

Patient D-4

Female, age 61, diagnosed with severe hyperlipidemia, small vessel coronary artery disease by cardiac catheterization, type 2 diabetes, hypertension and hypothyroidism, all of which were under medical management, including injectable Victoza® and Lantus® insulin for diabetes. Patient historically was statin intolerant with statin myalgia but multiple coronary risk factors and known coronary disease mandated LDL control. An earlier trial of simvastatin resulted in severe rhabdomyolysis with CPK in the 900-1000 IU/L range. Off statins, baseline LDL=212 with the atherogenic type B pattern on Vertical Auto Profile (VAP) (Atherotec Diagnostic Labs). A trial of Zetia® 10 mg daily+low dose Crestor® 5 mg daily was initiated but CPK rapidly climbed to >800 IU/L. This was accompanied by recurrence of severe statin myalgia involving both thighs and calves. Due to significant rhabdomyolysis, Crestor® was promptly discontinued. While off statins for several months, CPK remained elevated with slight improvement (down to 705 IU/L) but myalgia had completely receded off Crestor®. The patient exhibited asymptomatic post-statin myositis (CPK 1-10×ULN) at that time. Patient re-evaluated approx. four months later, at which point LDL had returned to baseline (>200 mg %) off low-dose Crestor®. At that time, combination therapy with relatively high dose Crestor®, 20 mg daily+Zetia® 10 mg daily +calcium HMB monohydrate, 2 g BID was initiated. Patient again re-evaluated 37 days later with repeat labs. Myalgia, previously continuous, had resolved except for very mild discomfort climbing stairs. She resumed her regular routine walking with a friend 1-2 miles without stopping for rest and experienced no leg discomfort with this activity. LDL had dropped to target at 49 and CPK had fallen to 277 IU/L (26-192) on the new regimen.

Five months later, some residual but mild leg discomfort persisted with a rise in CPK to 378 IU/L. At the time, patient D-4's diabetes, managed by an endocrinologist, was uncontrolled (fasting glucose>200 mg %). Because of data suggesting that the area under blood level curve for HMB is reduced when ingested with glucose, HMB free acid was substituted for calcium HMB monohydrate to improve absorption. The patient was re-evaluated ten days later, at which point D-4 stated that she "felt better" on the free acid form (2 gelcaps TID, total dose 3 g daily), with a drop in CPK to 257 IU/L after ten days. Of note, her fasting blood glucose dropped to 100 mg % during the same time interval with no alteration of diet or diabetes medication.

Patient E-5

Male, 69 years old, underwent coronary bypass surgery ten years prior, with a history of mixed type hyperlipidemia, type 2 diabetes, hypertension and prior inferior myocardial infarction. Patient had a history of statin intolerance and stopped statin therapy due to statin myalgia. He was otherwise compliant with all other medications.

Lipid panel obtained 9 months prior to enrollment revealed triglyceride levels exceeding 500 mg %, thereby obscuring LDL measurements. At that time, he was placed on fenofibrate to lower triglycerides and a repeat lipid profile 7 months later showed triglycerides reduced to 374, and an LDL=134. Unfortunately, he was fenofibrate intolerant and this medication was stopped. Statin therapy with pravastatin 20 mg daily was initiated thereafter with the objective of using a very hydrophilic/less lipophilic statin hoping that this would be less likely to cause statin myopathy. The patient promptly developed statin myalgia and stopped pravastatin.

When enrolled, the patient was no longer taking a statin and had persistent post-statin myalgia of the calves, despite statin withdrawal. He was given calcium HMB monohydrate, 2 g BID and instructed to resume pravastatin 1 week later. CPK after HMB treatment=110 IU/L (39-308). The bilateral calf myalgia resolved rapidly and completely on HMB.

Patient F-6

Male, 66 years old, with a history of percutaneous coronary intervention, right coronary artery, ten years prior. Medical problems include type 2a hypercholesterolemia, type 2 diabetes, and hypertension. The patient had history of paroxysmal supraventricular tachycardia (PSVT) (arrhythmia) for which he underwent successful radiofrequency ablation. Hyperlipidemia was treated with atorvastatin, 40 mg daily and Zetia®, 10 mg daily. At the time of enrollment, he complained of the onset of myalgia and short term memory loss after switching from pravastatin to atorvastatin to achieve target LDL. The myalgia involved the left shoulder, extending into the cervical region and occipital muscles of the skull. In addition to short term memory loss, the patient had difficulty writing script but no focal motor deficit. All symptoms were present 6 months dating from the time conversion to atorvastatin. Upon enrollment, the patient was placed on a regimen of atorvastatin, 40 mg daily, Zetia®, 10 mg daily, and calcium HMB monohydrate, 2 g BID. At 2-month follow-up, all myalgia had completely resolved. His wife also stated his short term memory loss had improved. Repeat LDL was 43 (three years prior, LDL had been 72 while taking Vytorin®, 10/40).

Patient G-7

Female, 70 years old, with type 2a hyperlipidemia, long-standing statin intolerance on multiple attempts, paroxysmal atrial fibrillation, PVC's with normal stress test and benign hypertension. One month prior to enrollment: cholesterol (total) 254, LDL=169, HDL=56 and TG's=147. At that time, the patient underwent coronary angiography for what appeared to be ischemic chest pain but no obstructive coronary artery disease (CAD) was found. The patient, after this episode, was concerned about her elevated LDL with the potential for future events and requested enrollment into the SIM pilot study. SIM in her case was present in the form of disabling myopathy with profound global weakness. Upon enrollment, G-7 resumed statin therapy after an interval of greater than four years. In addition, she began calcium HMB monohydrate, 2 g BID. Approximately four weeks later, the patient remained free of all symptoms of myalgia and muscle weakness. Repeat LDL=108, reduced from 169. CPK=39 IU/L (29-168).

Patient H-8

Female, age 76, with a primary diagnosis of atrial fibrillation, controlled on anti-arrhythmic medication. She carried a secondary diagnosis of type 2a hyperlipidemia, previously treated with simvastatin. This medication was stopped due to bilateral leg myalgia, fully resolving post-statin calcium HMB monohydrate, 2 g BID. On follow-up encounter one month later, the patient remained completely asymptomatic on this combination.

Patient J-10

Female, age 71, with mild-to-moderate non-obstructive coronary artery disease with type 2a hyperlipidemia, hypertension and hypothyroidism. All conditions were under control with medical therapy. Eight months prior to enrollment, the patient was placed on Lipitor®, 10 mg daily. Since initiating statin therapy, she experienced bilateral thigh achiness walking (especially through the mall) and climbing stairs.

She consulted an orthopedic surgeon but the symptoms became progressively worse. Upon enrollment, she was placed on calcium HMB monohydrate, 2 g BID and instructed to continue Lipitor®, 10 mg daily. At follow-up one month later, she stated there was complete resolution of bilateral thigh pain.

Patient K-11

64-year-old female with severe familial hyperlipidemia, originally with LDL levels>300 mg % and B pattern (VAP) with a prior history of statin-induced rhabdomyolysis. Upon enrollment, patient had an LDL=282, and coincidentally, CPK=282 IU/L (29-168) on a regimen consisting of Crestor®, 10, mg daily, Zetia®, 10 mg daily and Lovaza® 4 capsules daily. Although she was a medication failure at that dose, increasing the dose of Crestor® would only result in worsening rhabdomyolysis. She was placed on calcium HMB monohydrate, 2 g BID and Crestor® was increased to 20 mg daily. At follow-up 47 days later: LDL=139 (50% reduction) and CPK=191 IU/L (32% reduction). The patient remains pain-free and exercises (weights and cardio) on a near-daily basis.

Patient L-12

Female, age 82, with coronary disease and prior coronary angioplasty (PCI 1st diagonal, bare metal stent, five years prior to enrollment). She had a history of statin intolerance with very rapid onset with various statins. As an alternative, she was managed with Zetia®, 10 mg daily as monotherapy. This strategy effectively eliminated her statin myalgia, specifically severe myalgia of the calves. Upon enrollment, LDL=122, HDL=37 and triglycerides=261 on Zetia® +diet, still not at target. At that time, patient was placed on Crestor®, 5 mg daily+calcium HMB monohydrate, 2 g BID. Two months later, the patient was pain-free and remains asymptomatic to date. Follow-up labs at two months: LDL=100, triglycerides=193 and CPK=87 IU/L (29-168).

Patient M-13

54-year-old male who underwent a 2-vessel PCI/stent procedure approx. 1.5 years prior to enrollment (left anterior descending and right coronary arteries). He also had a history of peripheral vascular disease and underwent left superficial femoral artery angioplasty eight months prior to enrollment. Getting to target LDL was critical in this patient but was impeded by biomarker(+) statin intolerance. Seven months prior to enrollment, patient was on Zetia® monotherapy but off statins due to SIM, LDL=244. Once again he was placed on a statin (Crestor®) but leg myalgia returned and, upon enrollment, CPK had risen to 320 IU/L (39-308). Crestor® was continued, and calcium HMB monohydrate, 2 g BID was added. On this combination, repeat lab was obtained four months later: LDL=114 (53% reduction), CPK=210 IU/L (39-308, 34% reduction). All myalgia had resolved at the time of a follow-up five months after enrollment and patient remained asymptomatic/myalgia-free at least eight months after enrollment.

Patient N-14

Male, age 48, with historical hypercholesterolemia complicated by statin myopathy in the form of muscle weakness involving extremities rather than myalgia. Medical problems included dysmetabolic syndrome and benign hypertension. About three years prior to enrollment, a Vertical Auto Profile (VAP) panel (Atherotech) revealed an LDL=109, type B pattern (small, dense, more atherogenic particles). At that time, treatment consisted of Zetia®, 10 mg daily and Welchol®, 625 mg daily. Repeat LDL a year prior to enrollment was 107. Because of co-morbidity placing patient at higher risk for coronary artery disease (CAD), a statin agent (Livalo®, 1 mg daily) was added 8 months prior to enrollment. SIM with muscle weakness eventually developed. Two months prior to enrollment, Livalo® was reduced to 0.5 mg daily but without improvement. The patient, in his own words, had "trouble picking things up."

Upon enrollment, LDL=107, CPK=200 IU/L (30-200). Calcium HMB monohydrate, 2 g BID was added at that time and statin therapy was continued. 13 days later, symptoms of muscle weakness had resolved and patient was able to return to normal physical activity.

Patient O-15

Male, age 70, with severe multivessel coronary disease, having undergone multiple stent percutaneous coronary interventions (PCIs). Medical history includes hyperlipidemia type 2a, adult onset diabetes mellitus type 2, hypertension and statin intolerance in the form of bilateral quadriceps myalgia. The patient's statin intolerance was mildly but persistently biomarker positive. Because of his CAD history with multiple PCI's, the patient remained on statin therapy despite daily leg discomfort in return for optimal LDL control without further adverse cardiac events. Lab upon enrollment: CPK=274 IU/L (30-200), LDL=30, TG's=324, HDL=29. Concurrent meds: Zetia®, 10 mg daily, Crestor®, 5 mg on alternate days and Lovaza® 4 g daily. After four weeks on combined statin therapy and calcium HMB monohydrate, 2 g BID, there was complete resolution of all quadriceps/thigh pain. Lab 2 months post-enrollment: LDL=53 (at target), CPK=310 IU/L. Discussing elevated CPK with patient, it was learned that he was now engaged in a 5 days/week weight program (6 machines, 50 reps to failure). This program is likely to cause CPK spill secondary to muscle micro-trauma (similar to patient A-1). Patient advised to adhere to a weight program combined with more cardio with rest periods to allow recovery. He was also converted to HMB free acid, 1 g TID for the purpose of evaluating its tolerance and reportedly superior absorption. Three months post-enrollment, he remained completely symptom-free of statin myalgia/myopathy.

Patient P-16

63-year-old male with a history of severe multi-vessel coronary disease presenting as unstable angina who underwent 4-vessel coronary bypass surgery with left internal mammary artery approx. 3 years prior to enrollment. Medical history included hyperlipidemia 2a and paroxysmal atrial fibrillation. Lipid management post-coronary bypass included atorvastatin. About a year prior to enrollment, initial symptoms of statin myopathy appeared: bilateral thigh and hip adductor pain continuous at rest and with activity. Patient was converted to simvastatin without relief in symptoms.

Upon enrollment, patient was prescribed simvastatin+calcium HMB monohydrate, 2 g BID. Lab at that time: LDL=79, CPK=225 IU/L (35-245). Sixteen days after enrollment, patient no longer had any thigh pain but there was a persistent groin "stiffness" that disappeared after a cardio/treadmill workout. These residual symptoms are not truly typical of statin myalgia.

Example 3

In-Patient Treatment of Acute Rhabdomyolysis

HMB administration is used to treat acute rhabdomyolysis in an in-patient setting.

Acute rhabdomyolysis is a rare but extreme and potentially life-threatening disorder that can occur in all groups in a setting of dehydration, trauma, and in younger age groups, intense exercise. Statin agents have also been shown to cause acute massive rhabomyolysis syndrome (a form of statin myopathy) resulting in acute kidney failure and hemodialysis. At this time there is no known method of reversing rhabomyolysis apart from bed rest and hydration.

Protocol: measure patient's CPK; if value exceeds 10 times the upper limit of normal (200 IU/L, depending on laboratory-specific established normal range), initiate the following:
1. Admit to ICU;
2. Initiate IV 0.9% saline at 165 ml/hour;
3. Initiate HMB free acid (gel form), dose 6 g twice daily for 3 days;
4. Lab: CPK, BUN, creatinine, glucose and electrolytes every 12 hours for 3 days.

Outcome: Patients' CPK is reduced below 200 IU/L within 3 days.

Example 4

Treatment of Statin-Induced Short-Term Memory Loss with HMB

HMB administration is used to treat short-term memory loss, an unusual side effect resulting from statin administration. Patient F-6, described in the pilot study of Example 2, exhibited this side effect. In F-6's case, symptoms began shortly after starting atorvastatin and mostly resolved with the administration of HMB. Here, HMB is used to resolve similar short-term memory loss exhibited by patients taking statins.

Protocol: Patient describes short term memory loss after starting statin. Initiate the following steps:
1. Assess memory loss with standardized neuro-psychometric testing as baseline status;
2. Initiate calcium HMB monohydrate, 2 g twice daily; or calcium free acid gel, 1 g three times daily;
3. Continue statin therapy with no dose change;
4. Obtain baseline lab (lipid panel, CPK, liver function/metabolic profile) and repeat in 12 weeks;
5. Reassess memory status in 12 weeks repeating psychometric testing and comparing to baseline study.

Outcome: Patients exhibit reversal of some or all short-term memory loss by HMB treatment within two months. Comparison of pre- and post-therapy neuropsychometric testing will be statistically analyzed (chi-squared, p-value).

Example 5

Treatment of Statin-Induced Abnormal Liver Function Using HMB

Elevated liver function tests (LFTs) are common in statin users. The presence of elevated transaminases, commonly the transaminases alanine transaminase (ALT or SGPT) and aspartate transaminase (AST or SGOT), are indicators of liver damage. Terms for this condition include transaminasemia and transaminitis, Normal ranges for both ALT and AST are 8-40 U/L with mild transaminesemia noted to the upward numerical limit of 250 U/L. Here, HMB is administered to normalize abnormal liver function tests and reverse transaminitis.
Protocol: Protocol: Patient must exhibit ALT and AST levels in excess of twice the upper limit of normal to enrol. Once enrolled, initiate the following steps:
1. Initiate calcium HMB monohydrate, 2 g twice daily or HMB free acid (gel form), 1 g three times daily;
2. Continue statin agent with no dose change;
3. Repeat liver panel in 3 months and compare to baseline.

Outcome: LFTs return to normal (ALT/SGPT less than 40 U/L, AST/SGOT less than 40 U/L) within 3 months of beginning HMB treatment.

Example 6

Treatment of Statin-Induced Glucose Intolerance Using HMB

Glucose intolerance with hyperglycemia/increased risk for diabetes, probably related to insulin resistance, has been reported in statin users, especially lipophilic statins such as rosuvastatin, less so in hydrophilic statins such as pravastatin. Here, HMB administration is used to treat statin-related glucose intolerance.

Protocol: type 1, 1.5, and 2 diabetics with hemoglobin A1C at or exceeding 6.5% are eligible; also eligible are hyperglycemic/increased risk for diabetes patients not on diabetic treatment but with a hemoglobin A1C at or exceeding 5.7%; patients with critical value fasting blood glucose and hemoglobin A1C levels are excluded. Once enrolled, the following steps are initiated:
1. Continue statin and diabetic medications with dosages unchanged;
2. Initiate calcium HMB monohydrate, 2 g twice daily, or HMB free acid (gel form), 1 g three times daily;
3. Repeat fasting blood glucose and hemoglobin Al C in 3 weeks and 6 weeks;

Outcome: Patients exhibit reduction of hemoglobin A1C to levels below 6.5% in diabetics and 5.7% in hyperglycemics on dietary management (i.e., with increased risk for diabetes) within 6 weeks of beginning HMB treatment, along with fasting blood glucose less than 100 mg % for hyperglycemic/non-diabetic management patients and less than 130 mg % for diabetic patients.

Example 7

Treatment of statin-Related Cumulative Trauma Disorder Using HMB

Cumulative trauma disorder, also known as chronic overuse syndrome, is characterized by muscle damage due to performing repetitive activities over time. Statin users are particularly vulnerable to cumulative trauma disorder due to impaired ability to heal chronically micro-traumatized muscle. Here, HMB is used to treat cumulative trauma disorder.

Protocol: Patients are enrolled if they qualify with symptoms that include chronic muscle weakness and pain complemented by an occupation or lifestyle lending itself to chronic overuse syndrome (e.g., construction workers, etc.). All patients are currently on statins. Initial documentation of strength levels and pain severity are required. Pain is evaluated using the Verbal Numerical Rating Scale (VNRS). Strength is measured using the Manual Muscle Testing/5-point scale. Additionally, grip strength is measured using a dynamometer. Once enrolled, the following steps are initiated:
1. Obtain baseline lab including lipid panel and CPK-MM levels;
2. Continue statin with dose unchanged;
3. Continue repetitive activity in question at the same level of intensity;
4. Initiate calcium HMB monohydrate, 2 g twice daily, or HMB free acid (gel form, 1 g three times daily;

5. Re-evaluate pain severity and strength levels of patient three weeks and six weeks after enrollment, statistically comparing pain severity and strength levels against baseline (p-value, Chi-squared);
6. Repeat baseline lab six weeks after enrollment.

Outcome: Patients exhibit reduced pain severity and increased strength levels within 6 weeks of beginning HMB treatment.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A method for alleviating one or more side effects of statin administration, the method comprising supplementing statin administration with administration of a therapeutically effective amount of β-hydroxy β-methylbutyrate (HMB).

2. The method of claim 1, wherein the one or more side effects of statin administration are myopathic or myalgic side effects, short-term memory loss, elevated alanine transaminase (ALT) or aspartate transaminase (AST) levels, glucose intolerance, hyperglycemia, increased risk for diabetes, or cumulative trauma disorder.

3. The method of claim 1, wherein HMB is administered at a dosage of approximately 2.0 to 4.0 grams/day.

4. The method of claim 3, wherein HMB is administered at a dosage of approximately 3.0 grams/day.

5. The method of claim 4, wherein HMB is administered at a dosage of approximately 4.0 grams/day.

6. The method of claim 1, wherein HMB is administered 1 to 5 times per day.

7. The method of claim 6, wherein HMB is administered 3 times per day.

8. The method of claim 6, wherein HMB is administered 2 times per day.

9. The method of claim 1, wherein the statin is atorvastatin, cerivastatin, fluvastatin, lovastatin, mevastatin, pitavastatin, pravastatin, rosuvastatin, or simvastatin.

10. The method of claim 9, wherein the statin is rosuvastatin.

11. The method of claim 1, wherein HMB is administered as calcium HMB monohydrate.

12. The method of claim 1, wherein HMB is administered as HMB free acid.

13. A pharmaceutical formulation comprising a statin and a statin side effect-alleviating amount of β-hydroxy β-methylbutyrate (HMB).

14. The pharmaceutical formulation of claim 13, wherein the statin is atorvastatin, cerivastatin, fluvastatin, lovastatin, mevastatin, pitavastatin, pravastatin, rosuvastatin, or simvastatin.

15. The pharmaceutical formulation of claim 14, wherein the statin is rosuvastatin.

16. The pharmaceutical formulation of claim 13, wherein the formulation comprises statin and HMB at a ratio that is approximately 0.001 to 0.1 by weight.

17. The pharmaceutical formulation of claim 13, wherein the formulation comprises statin and HMB at a ratio that is approximately 0.01 by weight.

18. The pharmaceutical formulation of claim 13, comprising from about 1.0 gram to about 4.0 grams HMB.

19. The pharmaceutical formulation of claim 13, wherein HMB is calcium HMB monohydrate.

20. The pharmaceutical formulation of claim 13, wherein HMB is HMB free acid.

21. A method for treating acute rhabdomyolysis in a patient, the method comprising administering a therapeutically effective amount of β-hydroxy β-methylbutyrate (HMB) to the patient.

22. The method of claim 21, wherein HMB is administered at a dosage of about 6 grams/day to about 12 grams/day.

23. The method of claim 22, wherein HMB is administered at a dosage of about 12 grams/day.

24. The method of claim 23, wherein HMB is HMB free acid.

25. The method of claim 21, wherein HMB is administered for at least three days.

* * * * *